United States Patent [19]

Rohrbach et al.

[11] Patent Number: 4,748,237
[45] Date of Patent: May 31, 1988

[54] INCREASING CYCLODEXTRIN YIELDS BY THE ADDITION OF VARIOUS SOLUTES TO STARCH FEEDSTOCKS

[75] Inventors: Ronald P. Rohrbach, Forest Lake; Dale S. Scherl, Mt. Prospect, both of Ill.

[73] Assignee: UOP Inc., Des Plaines, Ill.

[21] Appl. No.: 36,725

[22] Filed: Apr. 10, 1987

[51] Int. Cl.$^4$ ............................................. C08B 37/16
[52] U.S. Cl. ................................................... 536/103
[58] Field of Search ........................................ 536/103

[56] References Cited

U.S. PATENT DOCUMENTS 2,845,417  7/1958  Kesler et al. ................... 536/103

OTHER PUBLICATIONS

J. Szejtli, *Starch*, 34, 379–85 (1982).
K. Horikoshi, *Process Biochemistry*, May 1979 (26–30).
M. Matzuzawa et al., *Die Starke*, 27, 410–13 (1975).

*Primary Examiner*—Joseph L. Schofer
*Assistant Examiner*—Peter D. Mulcahy
*Attorney, Agent, or Firm*—Thomas K. McBride; John F. Spears, Jr.; Eugene I. Snyder

[57] ABSTRACT

The yield of cyclodextrins formed in the hydrolysis of starch catalyzed by a cyclodextrin glycosyltransferase can be substantially increased by the addition of certain water-soluble solutes. Alcohols containing 1 to 6 carbon atoms form one such class, with ethanol and isopropyl alcohol being especially effective. Where an immobilized cyclodextrin glycosyltransferase is used yields of beta-cyclodextrin can be increased from approximately 20% to almost 40% using 15% isopropyl alcohol in a thinned starch feedstock, with glucose production being increased by only about 25%.

11 Claims, 3 Drawing Sheets

INCREASING CYCLODEXTRIN YIELDS BY THE ADDITION OF VARIOUS SOLUTES TO STARCH FEEDSTOCKS

BACKGROUND OF THE INVENTION

Cyclodextrins are cyclic molecules consisting of 1-4 linked alpha-D-glucopyranose monomeric units. The cyclodextrins containing 6-, 7-, and 8-membered rings, commonly known as alpha-, beta-, and gamma-cyclodextrin, respectively, are the most important cyclodextrins to date, possibly because of their availability relative to cyclodextrins of different ring size. The usefulness of these cyclodextrins arises from their ability to reversibly form inclusion complexes, or clathrates, with many types of compounds. Inclusion complexes arise when a host molecule, such as a cyclodextrin, has a structure containing an interior cavity into which guest molecules can bind by weak interactions such as van der Waal's forces. The latter are short range forces which are sufficiently strong to allow the formation of definite, generally solid complexes, but are sufficiently weak to permit ready dissociation of the complex to a host and guest molecule.

The cyclodextrins are doughnut-shaped molecules with an interior cavity whose size and shape is determined by the number of glucose units that make up the ring. In alpha-cyclodextrin the almost cylindrical cavity is approximately 7 angstroms deep and 5 angstroms in diameter. In beta-cyclodextrin the depth is the same but the diameter is 7 angstroms, and in gamma-cyclodextrin cavity is again 7 angstroms deep but is 9 angstroms in diameter. Cyclodextrins are soluble in water because of the many hydroxyl groups of the glucose subunits that surround the rim of the cavity. However, the interior of the cavities themselves are hydrophobic, and these hydrophobic cavities extract organic molecules from aqueous solution if the organic materials have the correct shape and hydrophobic character.

The complexing ability of cyclodextrins lends itself to various uses. For example, the cyclodextrins are used in encapsulating desirable flavors and fragrances which can then be stored for reasonably long periods of time and added to foods at their preparation. Reciprocally, cyclodextrins may be used in removing undesirable flavors and fragrances from food by complexing with them. Cyclodextrins also are used in the protection of foods against oxidation, photochemical degradation, and thermal decomposition. These and other uses have been summarized by J. Szejtli, *Starch*, 34, 379-385 (1982)

To date cyclodextrins have been prepared by treating starch with a cyclodextrin glycosyltransferase (CG) first at a high temperature to liquefy the starch, then at a lower temperature to form the cyclodextrins from the liquefied starch. Although many variations are possible all utilize a liquid starch of low dextrose equivalent (DE), less than about 4, as a substrate for the enzyme. The prior art methods have been described and summarized by K. Horikoshi, *Process Biochemistry*, May, 1979, 26-30, and by M. Matzuzawa et al., *Die Starke*, 27, 410-413 (1975).

The use of thinned starch, that is, a partially hydrolyzed starch, as a feedstock can obviate some of the difficulties experienced above in the case of an immobilized cyclodextrin glycosyltransferase (IMCG), but whether a soluble or immobilized cyclodextrin glycosyltransferase is used the present methods of cyclodextrin manufacture suffer from several serious inherent limitations which severely restrict cyclodextrin manufacture. In both cases the solids content of the feedstock is relatively low, which limits cyclodextrin productivity, i.e., the amount of cyclodextrin formed per unit time. The total cyclodextrin yield also is relatively low, with total conversions of starch below 50 percent, often in the range of 25-35 percent. The low cyclodextrin yield merely exacerbates the low productivity associated with the low feedstock solids. The low solids content of the feedstock necessary for present cyclodextrin manufacture also results in increased processing costs downstream, for the cyclodextrins necessarily will be formed in a relatively dilute solution, which requires the removal of relatively larger amounts of water in a cyclodextrin purification stage. And since the removal of water from the product is an energy-intensive operation this translates directly into increased production and costs.

Bacterial contamination of polysaccharide feedstocks for enzyme mediated processes is a common problem amenable to several convenient solutions. During the evaluation of one such solution serendipity bestowed its ammple bounty upon us when we observed that the addition of ethanol to a feedstock of starch as a bacterial inhibitor also caused a significant increase in cyclodextrin yield. A subsequent focused investigation then showed that the presence of a spectrum of water-soluble material in the feedstock had a beneficial effect on cyclodextrin yield, and in some cases that effect was profound. Still further investigation demonstrated that such added solutes not only increased cyclodextrin yield but also permitted the use of feedstocks with higher solids content, thereby increasing productivity and reducing processing costs. Thus, the addition of some water-soluble materials to a starch feedstock simultaneously prevents bacterial contamination, increases cyclodextrin yield, increases cyclodextrin productivity, and reduces cyclodextrin processing costs. When serendipity smiles inventors rejoice!

SUMMARY OF THE INVENTION

The purpose of the invention described and claimed herein is to increase the yield and productivity of cyclodextrin formed by hydrolysis of starch catalyzed by cyclodextrin glycosyltransferase. An embodiment comprises performing the hydrolysis in the presence of an effective amount of a cyclodextrin-enhancing water-soluble solute. In a more specific embodiment the solute is an organic alcohol containing up to about 6 carbon atoms. In a still more specific embodiment the alcohol is ethanol or isopropyl alcohol in an amount from about 5 to about 40% by volume. Other specific embodiments will be apparent from the following description.

DESCRIPTION OF THE INVENTION

Figure 1:
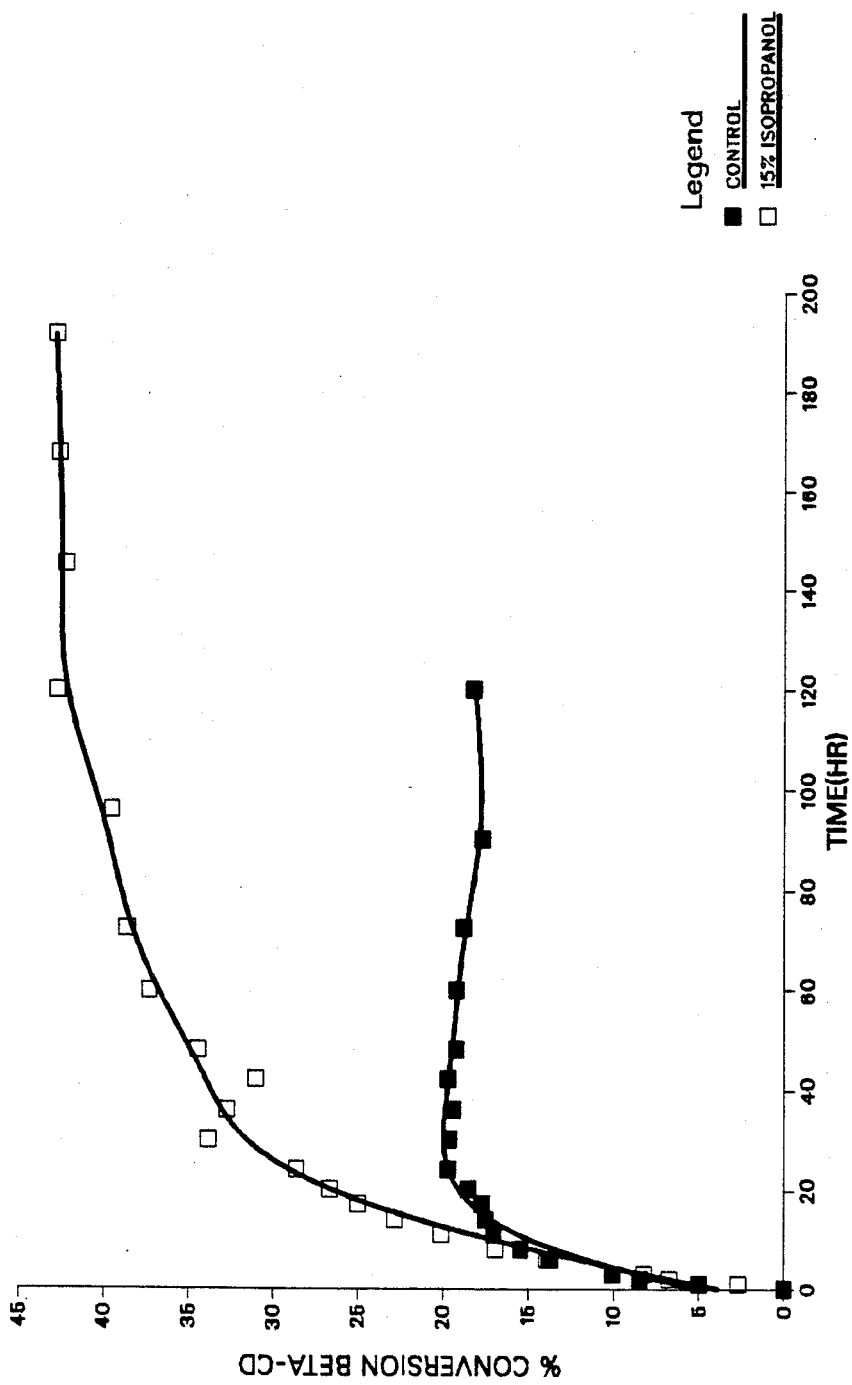
FIG. 1 shows the production of beta-cyclodextrin with time in the absence and presence of 15 volume percent isopropyl alcohol.

As a class of materials cyclodextrins have intriguing properties making them attractive for various commercial uses, as has been described above. However, production of cyclodextrin is plagued by low yields and low productivity. This invention increases both starch conversion to cyclodextrins as well as the amount of cyclodextrins formed per unit time using cyclodextrin glycosyltransferase to catalyze starch hydrolysis, and especially when using an immobilized cyclodextrin glycosyltransferase.

The feedstocks that are used for cyclodextrin production and which are used in the practice of this invention are aqueous starch solutions or suspensions, generally containing small amounts of other materials such as buffers, preservatives, etc. The feedstock may be raw starch, a liquified starch, or a thinned starch whose dextrose equivalent may be as low as about 0 and as high as about 40, although a feedstock with dextrose equivalent between about 2 and about 25 is preferred. The use of thinned starch is particularly favored where an immobilized cyclodextrin glycosyltransferase is used for starch hydrolysis, whereas traditionally this is not used with the soluble enzymes.

It is preferred that the starch feedstock have as high a solids content as possible to maximize the productivity of cyclodextrin production. However, one of the hydrolytic products is glucose, a known glycosyltransferase inhibitor, a fact which in the past has limited the dry solids content to a level under about 10%. In the practice of our invention a feedstock with a dry solids content between about 1 and at least about 30% may be used, with those having dry solids between about 2 and about 20% particularly recommended.

The cyclodextrin glycosyltransferase which is used to convert the starch to cyclodextrins may be used either as a soluble enzyme or as an immobilized enzyme. Where it is immobilized, the success of the invention does not depend upon the nature of the support matrix; it is intended that any support matrix may be used to immobilize cyclodextrin glycosyltransferase in the practice of our invention, and in this sense the IMCG referred to herein is a generic designation. This is not to say that the nature of the support matrix is immaterial but merely that any preference for a particular support matrix arises from factors incidental to and unconnected with this invention.

The results attending the addition of the solutes of our invention depend on the enzyme source. It appears that there are at least two classes of cyclodextrin glycosyltransferase. One class, as exemplified by the enzyme produced by $B.$ $circulans,$ can be characterized as a beta- and a low alpha-producer, for the mixture of cyclodextrins formed consists of approximately 5% alpha-, 20% beta-, and 2% gamma-cyclodextrin. On the other hand, a second class of enzymes, as exemplified by that produced from $B.$ $macerans,$ can be characterized as a high beta- and alpha-producing enzyme, for the cyclodextrins formed are about 17% alpha-, 17% beta-, and 5% gamma-cyclodextrin. In general, for the cyclodextrin glycosyltransferases of the first class the solutes of our invention tend to dramatically increase the beta-cyclodextrin, decrease the alpha-cyclodextrin, and cause a smaller increase in the gamma-cyclodextrin. In contrast, where a high alpha-producing enzyme is used the solutes of our invention primarily increase the yield of the alpha-cyclodextrin with little, or perhaps even a small negative, effect on beta-cyclodextrin production. It is clear then that the specific effect caused by the solutes of our invention will depend upon the particular enzyme used, but in all cases the total yield of cyclodextrins will be increased.

Our invention is based on the discovery that the addition of certain water-soluble materials to starch feedstock being hydrolyzed by cyclodextrin glycosyltransferase increases the yield of cyclodextrins formed. The solutes which are effective may be either organic solutes or salts. Among the favored organic solutes are alcohols containing from 1 through 6 carbon atoms, such as methanol, ethanol, and the isomeric propanols, butanols, pentanols, and hexanols. Alcohols containing 2, 3, or 4 carbon atoms are preferred, and both ethanol and isopropyl alcohol are highly recommended solutes in the practice of this invention. One reason why isopropyl alcohol is so highly recommended when used with certain cyclodextrin glycosyltransferases is that it substantially increases the yield of beta-cyclodextrin with a much smaller attendant increase in glucose formation. As was previously mentioned, glucose is an enzyme inhibitor, so that its formation is desirably minimized.

Other water soluble organic materials also can be used, including the lower ketones as ethyl ketone and methyl ethyl ketone. The class of organic solutes which may be used in the practice of this invention can be phenomenologically and operationally defined. First, they need to be soluble at least to the extent of about 5%, on a volume-volume basis where the solute is a liquid and a weight-volume basis where the solute is solid, at 50° C. Secondly, they must complex with one or more of the cyclodextrins, but the complex must be soluble in the reaction mixture under reaction conditions. The solute also should have no detrimental effect on the stability of the enzyme as evidenced by its half-life or otherwise adversely affect enzyme performance. It is also important that the solute be readily separable from the cyclodextrins which are subsequently isolated, and it is preferable that the solutes themselves be approved for food use, at least at the low levels at which they are contemplated to accompany the isolated cyclodextrin.

As previously stated, salts also may be used in the practice of this invention so long as they conform to the phenomenological and operational definitions stated above. It has been found that the effect of salts of solutes is virtually independent of the cation in the salt, which implies that the cyclodextrin-enhancing properties arise only from the anion. This is consistent with the known complexing tendencies of cyclodextrins. Among the anions which may be used are included the halides, especially iodide, bromide, and to a lesser extent chloride, perchlorate, thiocyanate, and the oxoanions of pentavalent phosphorus, such as phosphate, hydrogen phosphate, dihydrogen phosphate, pyrophosphate, etc. When salts are used in the practice of this invention they may be used at a concentration between about 0.1M to about 2M. Where organic solutes are used it has been found that they are effective at a concentration between about 5 and about 40%, although normally their concentration does not exceed about 30%, where percentages are volume-volume or weight-volume depending upon whether the solute is liquid or solid, respectively.

Other than the presence of the solutes of this invention, there is no difference in the conditions under which starch hydrolysis to cyclodextrins is conducted.

Thus, hydrolysis generally is performed at a temperature between about 45° and about 70° C., even more usually between about 50° and about 60° C. The starch feedstock generally is buffered with the hydrolysis being performed at a pH between roughly 5.5 and 7.5. In any event, the conditions for hydrolysis of starch to cyclodextrins as catalyzed by cyclodextrin glycosyltransferase are well known to those in the art and need not be further discussed here.

The examples which follow are only illustrative of this invention and do not limit it in any significant way. Unless otherwise stated, the cyclodextrin glycosyltransferase was obtained from Bacillus circulans. Its immobilization typically was carried out in the following way.

To 1.0 g of beta-alumina (60/80 mesh) was added 10.0 mL of a 1.8% aqueous solution of polyethyleneimine (PEI) at pH 10.5. Impregnation of the agitated mixture was continued for 1 hour under vacuum at room temperature and the PEI-coated support thereafter separated by filtration, then allowed to air dry at room temperature for 2 days. To this PEI-coated support was added 10.0 mL of a 5.0% aqueous solution of glutaraldehyde. Excess liquid was removed by decantation and solid was washed copiously with deionized water to remove excess glutaraldehyde. Washing was continued until the filtrate gave a negative Fuchsin test, after which it was washed 3-4 times with a 1 millimolar sodium acetate buffer at pH 5.0.

A solution of purified cyclodextrin glycosyltransferase was adjusted to pH 5.0 by addition of 1.0 molar sodium acetate. To the activated supported prepared as described above was added the solution of glycosyltransferase and the mixture was shaken on an orbital shaker at 4° C. overnight with a cycle of 15 seconds on and 5 minutes off. Excess liquid then was removed by decantation and the immobilized enzyme preparation was washed well in order to remove adhering but unbound enzyme.

Soluble cyclodextrin glycosyltransferase was assayed using a substrate of 0.2% soluble starch at pH 7.0 containing calcium chloride (5 millimolar) and imidazole (100 millimolar). To 0.30 mL of the substrate maintained in a 40° C. water bath was added 10 microliters of an enzyme solution. After 10 minutes the reaction is quenched with 4.0 mL of 0.2 molar hydrochloric acid, and there is added 0.5 mL of a solution containing 0.02% iodine and and 0.20% of potassium iodide. At the same time a control is prepared using 0.30 mL of the substrate to which is added 4.0 mL of 0.2 molar hydrochloric acid followed by 10 microliters of the enzyme solution whose activity is being assayed and 0.5 mL of the I$_2$-KI solution. The absorbance at 700 nanometers was then measured on both the control and the sample with activity calculated according to the equation, $$\text{Activity (units/mL)} = \frac{[OD(\text{control}) - OD(\text{sample})] \times 100}{OD(\text{control}) \times 0.01}$$

The difference in absorbance between the control and sample must be between 0.1 and 0.4 absorbance units. If values are not within this range, the enzyme solution is diluted and such dilutions are then factored into the calculation.

EXAMPLE I

Effect of ethanol.

In an effort to reduce microbial contamination, 4% by volume of ethanol was added to partially hydrolyzed starch, D.E. 15, 2% dry solids which also contained calcium chloride (5 mM) and imidazole (5 mM) and used as the feedstock for an IMCG at 50° C. In addition to the feedstock being contamination free over a period of 19 days, the amount of beta-cyclodextrin formed was increased from 15 to 25%. There also was observed no significant change in the stability of the catalyst after 19 days.

As a result of the preceding observation a scan of the effect of ethanol on the formation of cyclodextrins was performed in the following way. The feedstock described above containing various amounts of ethanol was used as the feedstock for soluble cyclodextrin glycosyltransferase. The amount of each cyclodextrin was determined by high pressure liquid chromatography under conditions where there was complete resolution of the alpha-, beta-, and gamma-cyclodextrins. The following table summarizes these results.

TABLE 1

| Effect of Ethanol Concentration on Cyclodextrin Production | | | |
|---|---|---|---|
| % Ethanol[a] | Alpha[b] | Beta[b] | Gamma[b] |
| 0 | 0.156 | 0.321 | 0.009 |
| 5 | 0.165 | 0.392 | 0.012 |
| 10 | 0.133 | 0.474 | 0.029 |
| 15 | 0.096 | 0.527 | 0.031 |
| 20 | 0.074 | 0.572 | 0.032 |
| 25 | 0.048 | 0.572 | 0.045 |
| 40 | 0.030 | 0.647 | 0.060 |

[a]Volume percent
[b]Concentration in weight percent.

As these data show, the amount of beta-cyclodextrin formed increases appreciably with the amount of ethanol added. The most significant changes appear to occur in the range up to about 25 volume percent ethanol.

EXAMPLE 2

Effect of Organic Solutes.

The feedstocks used were a 2.0 weight percent solution of partially hydrolyzed starch, D.E. 15, at pH 7.0 5 mM in both CaCl$_2$ and imidazole and containing varying amounts of organic solutes. To 1.0 ml feedstock was added 10 microliters of an enzyme solution and the reaction at 40° C. was continued for 1 hour. The solution was quenched by heating to boiling and then was analyzed by HPLC as described above. Results are summarized in the following table.

TABLE 2

| Effect of Some Organic Solutes on Beta-cyclodextrin formation. | | |
|---|---|---|
| Solute | Concentration[a] | Beta-cyclodextrin[b] |
| None |  | 18.6 |
| ethanol | 5 | 23.0 |
| 2-propanol | 5 | 29.1 |
| isobutyl alcohol | 5 | 28.8 |
| sec-butyl alcohol | 5 | 32.1 |
| tert-butyl alcohol | 5 | 35.8 |
| none |  | 18.7 |
| methanol | 20 | 21.0 |
| ethanol | 20 | 24.4 |
| 2-propanol | 20 | 25.6 |
| acetone | 20 | 30.2 |

[a]Concentration is in volume-volume percent
[b]Concentration is in weight percent relative to starch conversion These results show that the lower alcohols, as a class, are effective in increasing the yield of beta-cyclodextrin, but that the effects of the alcohols depend both upon the nature of the alcohol and of their concentration. Using tert-butyl alcohol as a solute at 5 volume percent approximately doubles the yield of beta-cyclodextrin.

EXAMPLE 3

Effect of isopropyl alcohol on beta-cyclodextrin and glucose production using IMCG.

Figure 2:
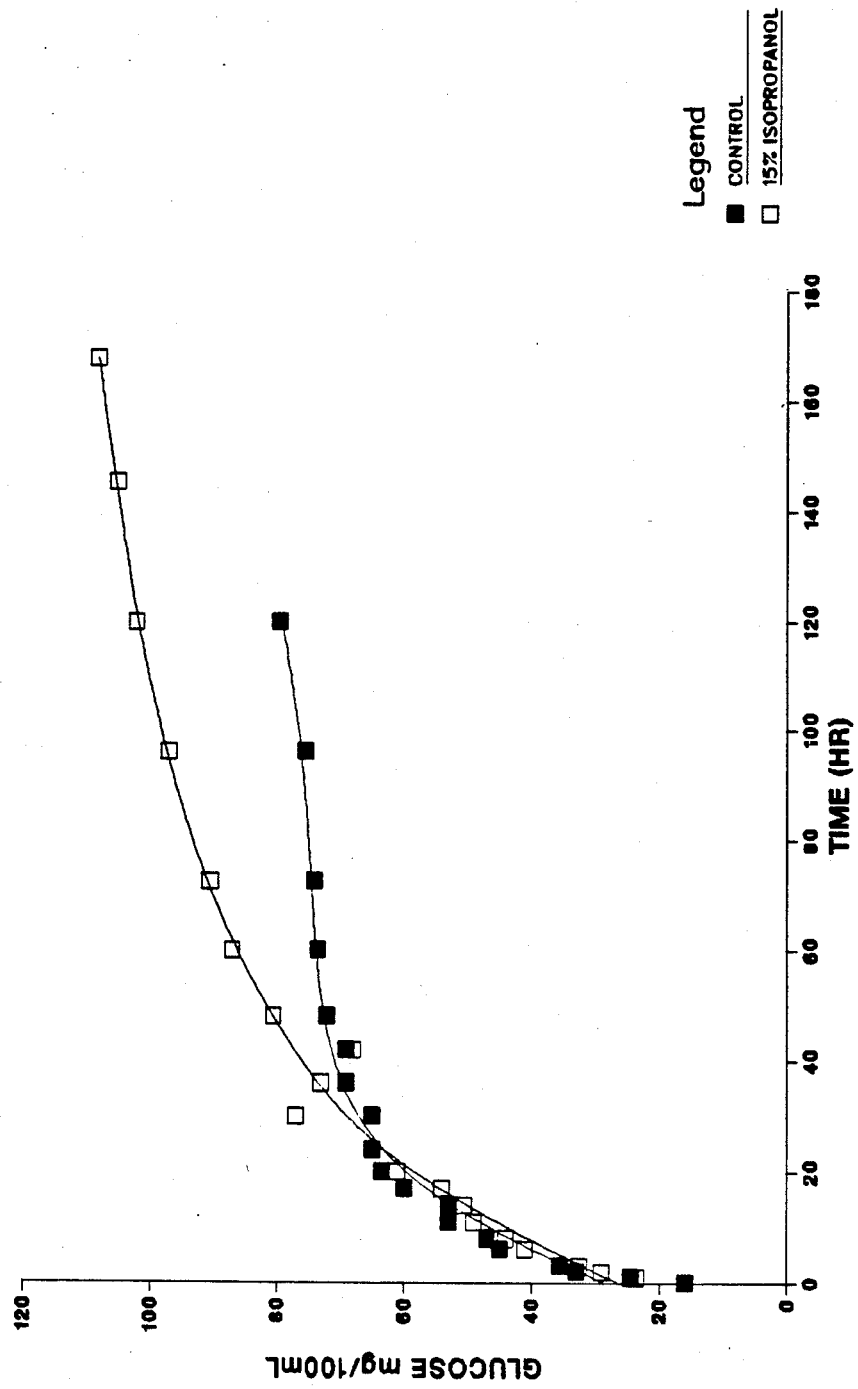
FIG. 2 shows the production of glucose with time in the absence and presence of 15 volume percent isopropyl alcohol.

A feedstock of 2 weight percent partially hydrolyzed starch of D.E. 15 (Maltrin 150) containing 15 volume percent isopropyl alcohol and 5 millimolar in both calcium chloride and imidazole, buffered to pH 7.0, was used in a batch recycle mode with IMCG. FIGS. 1 and 2 show the time course of both beta-cyclodextrin and glucose formation. These data show that relative to the control, addition of isopropyl alcohol at 15 volume percent roughly doubles the yield of cyclodextrin. It is also important to note that the glucose yield is increased on the order of only about 30%. Since glucose is an inhibitor for cyclodextrin glycosyltransferase, this lower increase in glucose production relative to beta-cyclodextrin formation means that the latter gain is accompanied with only a small inhibitory "penalty".

EXAMPLE 4

Effect of ethanol and isopropyl alcohol on beta-cyclodextrin formation using IMCG.

Figure 3:
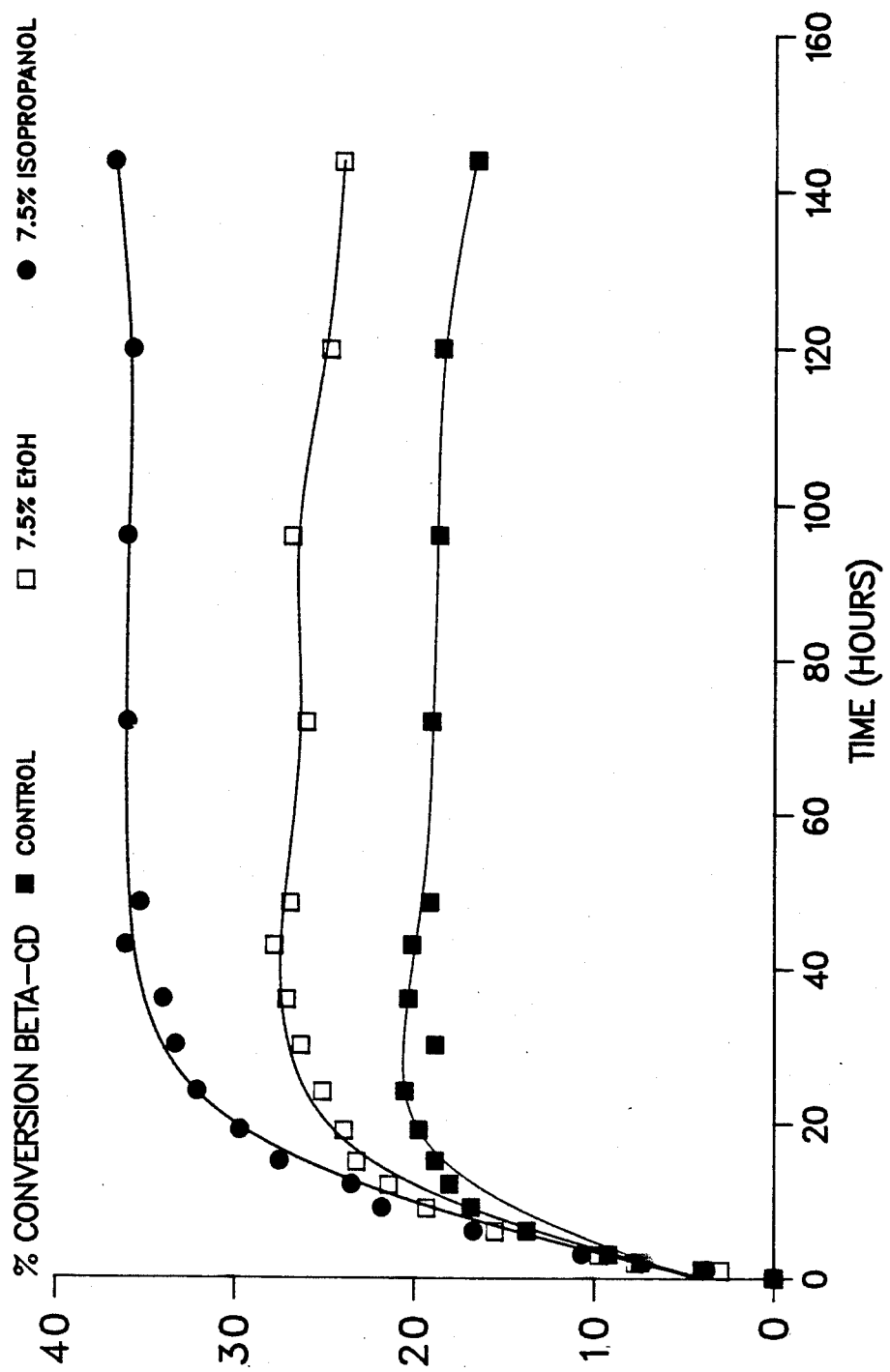
FIG. 3 shows the time course of beta-cyclodextrin in the presence of 7.5 volume percent ethanol or isopropyl alcohol.

Experiments similar to that described in the previous example were performed using 7.5 volume percent ethanol and isopropyl alcohol as the added solute. The time course of maximum beta-cyclodextrin production is shown in FIG. 3. The figure there shows that ethanol increases beta-cyclodextrin from about 19 to about 25%, whereas 7.5 volume percent isopropyl alcohol raises it to about 36%.

EXAMPLE 5

Effect of ionic strength on beta-cyclodextrin formation.

The effect of various concentrations of sodium sulfate on beta-cyclodextrin formation using soluble enzyme and a feedstock of 2% of a partially hydrolyzed starch of D.E. 15, at a pH of 7.0 was determined with the results summarized in the following table.

TABLE 3

| Salt Concentration and Beta-cyclodextrin Formation | |
|---|---|
| $Na_2SO_4$ Molarity | Percent Beta-cyclodextrin Yield |
| 0 | 18.0 |
| 0.1 | 17.8 |
| 0.2 | 17.6 |
| 0.3 | 16.7 |
| 0.4 | 16.1 |
| 0.5 | 15.7 |

These results show that ionic strength with a non-complexing anion has a negative effect on beta-cyclodextrin formation.

EXAMPLE 6

Effect of certain anions on beta-cyclodextrin formation.

The effect of various inorganic anions on beta-cyclodextrin yield was determined as described in the previous example using the specified salts added in the amount indicated. Results are summarized in the accompanying table which shows an increase in beta-cyclodextrin formation relative to that formed in the presence of sodium sulfate alone.

TABLE 4

| Comparative Effect of Halid Salts | |
|---|---|
| Salt, molarity | Percent beta-cyclodextrin yield |
| — | 17.3 |
| $Na_2SO_4$, 1.0 M | 14.0 |
| KCl, 1.0 M | 17.4 |
| KI, 1.0 M | 20.9 |

We claim:

1. In the method of making cyclodextrins by hydrolyzing a feedstock of starch in the presence of a cyclodextrin glycosyltransferase, the improvement comprising performing the hydrolysis in the presence of an effective amount of a cyclodextrin-enhancing water-soluble solute selected from the group consisting of: organic solutes at a concentration from about 5 to about 40%; salts of oxoanions, said oxoanion being selected from the group consisting of halide, perchlorate, thiocyanate, and oxoanions of pentavalent phosphorus, at a concentration from 0.1 to about 2 molar; and combinations thereof.

2. The method of claim 1 where the hydrolysis is mediated by a soluble cyclodextrin glycosyltransferase.

3. The method of claim 1 where the hydrolysis is mediated by an immobilized cyclodextrin glycosyltransferase.

4. The method of claim 1 where the solute is an alcohol containing up to about 6 carbon atoms.

5. The method of claim 4 where the alcohol is ethanol, a propanol, or a butanol.

6. The method of claim 1 where the feedstock is a partially hydrolyzed starch of dextrose equivalent between about 0 and about 40.

7. The method of claim 6 where the dextrose equivalent is between about 2 and about 25.

8. The method of claim 4 where the alcohol is present in an amount from about 5 to about 30%.

9. The method of claim 1 where the feedstock is a partially hydrolyzed starch of dextrose equivalent from about 2 to about 25 containing from about 5 to about 30% by volume of ethanol or isopropyl alcohol and the hydrolysis is performed by an immobilized cyclodextrin glycosyltransferase.

10. The method of claim 1 further characterized in that the solute primarily increases the yield of beta-cyclodextrin.

11. The method of claim 10 where the solute is added in an amount sufficient to increase the yield of beta-cyclodextrin by at least 30%.

* * * * *